United States Patent [19]
Sih

[11] 4,264,522
[45] Apr. 28, 1981

[54] 19-HYDROXY-PG AMIDES

[75] Inventor: John C. Sih, Kalamazoo, Mich.

[73] Assignee: The Upjohn Company, Kalamazoo, Mich.

[21] Appl. No.: 88,501

[22] Filed: Oct. 26, 1979

Related U.S. Application Data

[62] Division of Ser. No. 25,899, Apr. 2, 1979, Pat. No. 4,228,104.

[51] Int. Cl.³ ............... C07C 177/00; C07C 103/19; C07C 143/16
[52] U.S. Cl. .................... 564/189; 424/320; 424/321; 424/324; 564/91; 564/95; 564/98; 564/99; 564/169; 564/171; 564/174
[58] Field of Search .......... 260/557 R, 558 R, 558 P, 260/559 R, 559 B, 556 AC

[56] References Cited

U.S. PATENT DOCUMENTS

| 3,954,741 | 5/1976 | Schaaf et al. | 542/426 |
| 4,054,595 | 10/1977 | Marx et al. | 260/438.1 |
| 4,098,805 | 7/1978 | Bundy | 542/426 |
| 4,127,612 | 11/1978 | Kluender et al. | 260/438.1 |
| 4,152,527 | 5/1979 | Hess et al. | 542/426 |

OTHER PUBLICATIONS

Sih, Prostaglandins, 13(5), 1977, pp. 831–835.

*Primary Examiner*—Arthur P. Demers
*Attorney, Agent, or Firm*—Robert A. Armitage

[57] ABSTRACT

The present invention provides novel 19-hydroxy-PG amides methods for their preparation and pharmacological use for the induction of prostaglandin-like effect.

263 Claims, No Drawings

19-HYDROXY-PG AMIDES

CROSS REFERENCE TO RELATED APPLICATIONS

The present application is a division of Ser. No. 025,899, filed Apr. 2, 1979, now U.S. Pat. No. 4,228,104.

BACKGROUND OF THE INVENTION

The present invention relates to novel prostaglandin analogs. Particularly, these compounds are analogs of the prostaglandins wherein the C-19 position is substituted by hydroxy, i.e., 19-hydroxy-PG compounds. Most particularly, the present invention relates to novel 19-hydroxy-PG amides, a disclosure of the preparation and use of which is incorporated here by reference from U. S. Pat. No. 4,228,104.

Prior Art

Prostaglandin analogs exhibiting hydroxylation in the 19-position are known in the art. See, for example, U.S. Pat. No. 4,127,612, SiH, J.C., Prostaglandins 13:831 (1977) and U.S. Pat. Nos. 3,657,316, 3,878,046, and 3,922,297. See also the additional references cited in U.S. Ser. No. 025,899.

SUMMARY OF THE INVENTION

The present invention particularly provides:
A compound of the formula

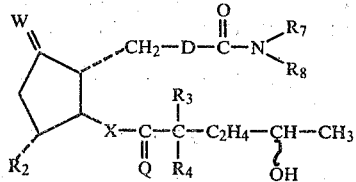

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)$_3$—CH=CH—,
(5) —(CH$_2$)$_3$—(CH$_2$)$_g$—CH$_2$—,
(6) —(CH$_2$)$_3$—CH$_2$—CF$_2$—,
(7) —(CH$_2$)$_3$—O—CH$_2$—,
(8) —(CH$_2$)$_2$—O—(CH$_2$)$_2$—,
(9) —CH$_2$—O—(CH$_2$)$_3$—,
(10) (m—ph) (CH$_2$)$_2$—, or
(11) (m—ph)—O—CH$_2$—
wherein m—Ph is inter-meta-phenylene, and wherein g is zero, one, two, or three; wherein Q is α—OH:β—R$_5$ or α—R$_5$:β—OH,
wherein R$_5$ is hydrogen or methyl, wherein one of R$_7$ and R$_8$ is hydrogen and the other is —SO$_2$R$_{29}$ or
wherein R$_7$ and R$_8$ are hydrogen, alkyl of one to 12 carbon atoms, inclusive, benzyl, or phenyl, being the same or different; wherein R$_{29}$ is hydrogen, alkyl of one to 12 carbon atoms, inclusive, aralkyl of 7 to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl of one to 4 carbon atoms, inclusive; wherein R$_2$ is hydrogen, hydroxyl, or hydroxymethyl; wherein R$_3$ and R$_4$ are hydrogen, methyl, or fluoro, being the same or different, with the proviso that one of R$_3$ and R$_4$ is fluoro only when the other is hydrogen or fluoro; wherein W is oxo, methylene, α—OH:β—H, or α—H:β—OH; and wherein X is cis- or trans—CH=CH—, —C≡C—, or —CH$_2$CH$_2$—.

With regard to the divalent the substituents described above (e.g., Q) these divalent radicals are defined as α—R$_I$:β—R$_J$, wherein R$_I$ represents the substituent of the divalent moiety in the alpha configuration with respect to the ring and R$_j$ represents the substituent of the divalent moiety in the beta configuration with respect to the plane of the ring. Accordingly, when Q is defined as α—OH:β—R$_5$, the hydroxy of the Q moiety is in the alpha configuration, i.e., as in the natural prostaglandin, and the R$_5$ substituent is in the beta configuration.

Specific embodiments of the present invention include:
19(R)-19-hydroxy-PGF$_{2\alpha}$, amide,
11-deoxy-19(R)-19-hydroxy-PGF$_{2\alpha}$, amide,
11-deoxy-11α-hydroxymethyl-19(R)-19-hydroxy-PGF$_{2\alpha}$, amide,
19(R)-19-hydroxy-PGF$_{2\beta}$, amide,
11-deoxy-19(R)-hydroxy-PGF$_{2\beta}$, amide,
11-deoxy-11α-hydroxymethyl-19(R)-19-hydroxy-PGF$_{2\beta}$, amide,
19(R)-19-hydroxy-PGE$_2$, amide,
11-deoxy-19(R)-19-hydroxy-PGE$_2$, amide,
11-deoxy-11α-hydroxymethyl-19(R)-19-hydroxy-PGF$_2$. amide,
9-deoxo-9-methylene-19(R)-19-hydroxy-PGE$_2$, amide,
9-deoxo-9-methylene-11-deoxy-19(R)-19-hydroxy-PGE$_2$, amide,
9-deoxo-9-methylene-11-deoxy-11α-hydroxymethyl-19(R)-19-hydroxy-PGE$_2$, amide,
4,5-didehydro-19(R)-19-hydroxy-PGF$_{1\alpha}$, amide,
4,5-didehydro-19(R)-19-hydroxy-15(S)-15-methyl-PGF$_{1\alpha}$, amide,
4,5,13,14-tetradehydro-19(R)-19-hydroxy-PGF$_{1\alpha}$, amide,
4,5,13,14-tetradehydro-19(R)-19-hydroxy-16,16-difluoro-PGF$_{1\alpha}$, amide,
4,5-didehydro-19(R)-19-hydroxy-11-deoxy-PGF$_{1\alpha}$, amide,
4,5-didehydro-19(R)-19-hydroxy-11-deoxy-15(S)-15-methyl-PGF$_{1\alpha}$, amide,
4,5,13,14-tetradehydro-19(R)-19-hydroxy-11-deoxy-PGF$_{1\alpha}$, amide,
4,5,13,14-tetradehydro-19(R)-19-hydroxy-11-deoxy-16,16-difluoro-PGF$_{1\alpha}$, amide,
4,5-dideoxy-19(R)-19-hydroxy-11-deoxy-11α-hydroxymethyl-PGF$_{1\alpha}$, amide,
4,5-dideoxy-19(R)-19-hyroxy-11-deoxy-11α-hydroxymethyl-15(S)-15-methyl-PGF$_{1\alpha}$, amide,
4,5,13,14-tetradehydro-19(R)-19-hydroxy-11-deoxy-11αhydroxymethyl-PGF$_{1\alpha}$, amide,
4,5,13,14-tetradehydro-19(R)-19-hydroxy-11-deoxy-11α-hydroxymethyl-16,16-difluoro-PGF$_{1\alpha}$, amide,
4,5-didehydro-19(R)-19-hydroxy-PGF$_{1\beta}$, amide,
4,5-didehydro-19(R)-19-hydroxy-15(S)-15-methyl-PGF$_{1\beta}$, amide,
4,5,13,14-tetradehydro-19(R)-19-hydroxy-PGF$_{1\beta}$, amide,
4,5,13,14-tetradehydro-19(R)-19-hydroxy-16,16-difluoro-PGF$_{1\beta}$, amide,
4,5-didehydro-19(R)-19-hydroxy-11-deoxy-PGF$_{1\beta}$, amide,
4,5-didehydro-19(R)-19-hydroxy-11-deoxy-15(S)-15-methyl-PGF$_{1\beta}$, amide, 4,5,13,14-tetradehydro-19(R)-19-hydroxy-11-deoxy-PGF$_{1\beta}$, amide,
4,5,13,14-tetradehydro-19(R)-19-hydroxy-11-deoxy-16,16-difluoro-PGF$_{1\beta}$, amide,
4,5-didehydro-19(R)-19-hydroxy-11-deoxy-11α-hydroxy-methyl-PGF$_{1\beta}$, amide,
4,5-didehydro-19(R)19-hydroxy-11-deoxy-11α-hydroxy-methyl-15(S)-15-methyl-PGF$_{1\beta}$, amide,
4,5,13,14-tetradehydro-19(R)-19-hydroxy-11-deoxy-11α-hydroxymethyl-PGF$_{1\beta}$, amide,
4,5,13,14-tetradehydro-19(R)-19-hydroxy-11-deoxy-11α, hydroxymethyl-16,16-difluoro-PGF$_{1\beta}$, amide,
4,5-didehydro-19(R)-19-hydroxy-PGE$_1$, amide,
4,5-didehydro-19(R)-19-hydroxy-15(S)-15-methyl-PGE$_1$, amide,
4,5,13,14-tetradehydro-19(R)-19-hydroxy-PGE$_1$, amide,
4,5,13,14-tetradehydro-19(R)-19-hyroxy-16,16-difluoro-PGE$_1$, amide,
4,5-didehydro-19(R)-19-hydroxy-11-deoxy-PGE$_1$, amide,
4,5-didehydro-19(R)-19-hydroxy-11-deoxy-15(S)-15-methyl-PGE$_1$, amide,
4,5,13,14-tetrahydro-19(R)-19-hydroxy-11-deoxy-PGE$_1$, amide,
4,5,13,14-tetradehydro-19(R)-19-hydroxy-11-deoxy-16,16-difluoro-PGE$_1$, amide,
4,5-didehydro-19(R)-19-hydroxy-11-deoxy-11α-hydroxymethyl-PGE$_1$, amide,
4,5-didehydro-19(R)-19-hydroxy-11-deoxy-11α-hydroxymethyl-15(S)-15-methyl-PGE$_1$, amide,
4,5,13,14-tetradehydro-19(R)-19-hydroxy-11-deoxy-11α-hydroxymethyl-PGE$_1$, amide,
4,5,13,14-tetradehydro-19(R)-19-hydroxy-11-deoxy-11α-hydroxymethyl-16,16-difluoro-PGE$_1$, amide,
4,5-didehydro-19(R)-19-hydroxy-9-deoxo-9-methylene-PGE$_1$, amide,
4,5-didehydro-19(R)-19-hydroxy-9-deoxo-9-methylene-15(S)-15-methyl-PGE$_1$, amide,
4,5,13,14-tetradehydro-19(R)-19-hydroxy-19-deoxo-9-methylene-PGE$_1$, amide,
4,5,13,14-tetradehydro-19(R)-19-hydroxy-9-deoxo-9-methylene-16,16-difluoro-PGE$_1$, amide,
4,5-didehydro-19(R)-19-hydroxy-9-deoxo-9-methylene-11-deoxy-PGE$_1$, amide,
4,5-didehydro-19(R)-19-hydroxy-9-deoxo-9-methylene-15(S)-15-methyl-PGE$_1$, amide,
4,5,13,14-tetradehydro-19(R)-19-hydroxy-9-deoxo-9-methylene-11-deoxy-PGE$_1$, amide,
4,5,13,14-tetradehydro-19(R)-19-hydroxy-9-deoxo-9-methylene-11-deoxy-16,16difluoro-PGE$_1$, amide,
4,5-didehydro-19(R)-19-hydroxy-9-deoxo-9-methylene-11-deoxy-11α-hydroxymethyl-PGE$_1$, amide,
4,5-didehydro-19(R)-19-hydroxy-9-deoxo-9-methylene-11-deoxy-11α-hydroxymethyl-15(S)-15-methyl-PGE$_1$, amide,
4,5,13,14-tetradehydro-19(R)-19-hydroxy-9-deoxo-9-methylene-11-deoxy-11α-hydroxy-methyl-PGE$_1$, amide,
4,5,13,14-tetradehydro-19(R)-19-hydroxy-9-deoxo-9-methylene-11-deoxy-11α-hydroxmethyl-16,16-difluoro-PGE$_1$, amide,
2,3-didehydro-19(R)-19- hydroxy-PGF$_{1\alpha}$, amide,
2,3-didehydro-19(R)-19-hydroxy-16,16-difluoro-PGF$_{1\alpha}$, amide,
2,3-didehydro-19(R)-19-hydroxy-15(S)-15-methyl-PGF$_{1\alpha}$, amide,
2,3-didehydro-19(R)-19-hydroxy-11-deoxy-PGF$_{1\alpha}$, amide,
2,3-didehydro-19(R)-19-hydroxy-11-deoxy-16,16-difluoro-PGF$_{1\alpha}$, amide,
2,3-didehydro-19(R)-19-hydroxy-11-deoxy-15(S)-15-methyl-PGF$_{1\alpha}$, amide,
2,3-didehydro-19(R)-19-hydroxy-11-deoxy-11α-hydroxymethyl-PGF$_{1\alpha}$, amide,
2,3-didehydro-19(R)-19-hydroxy-11-deoxy-11α-hydroxymethyl-16,16-difluoro-PGF$_{1\alpha}$, amide,
2,3-didehydro-19(R)-19-hydroxy-11-deoxy-11α-hydroxymethyl-15(S)-15-methyl-PGF$_{1\alpha}$, amide,
2,3-didehydro-19(R)-19-hydroxy-PGF$_{1\beta}$, amide,
2,3-didehydro-19(R)-19-hydroxy-16,16-difluoro-PGF$_{1\beta}$, amide,
2,3-didehydro-19(R)-19-hydroxy-15(S)-methyl-PGF$_{1\beta}$, amide,
2,3-didehydro-19(R)-19-hydroxy-11-deoxy-PGF$_{1\beta}$, amide
2,3-didehydro-19(R)-19-hydroxy-11-deoxy-16,16-difluoro-PGF$_{1\beta}$, amide,
2,3-didehydro-19(R)-19-hydroxy-11-deoxy-15(S)-15-methyl-PGF$_{1\beta}$, amide,
2,3-didehydro-19(R)-19-hydroxy-11-deoxy-11α-hydroxymethyl-PGF$_{1\beta}$, amide,
2,3-didehydro-19(R)-19-hydroxy-11-deoxy-11α-hydroxymethyl-16,16-difluoro-PGF$_{1\beta}$, amide,
2,3-didehydro-19(R)-19-hydroxy-11-deoxy-11α-hydroxymethyl-15(S)-15-methyl-PGF$_{1\beta}$, amide,
2,3-didehydro-19(R)-19-hydroxy-PGE$_1$, amide,
2,3-didehydro-19(R)-19-hydroxy-16,16-difluoro-PGE$_1$, amide,
2,3-didehydro-19(R)-19-hydroxy-15(S)-15-methyl-PGE$_1$, amide,
2,3-didehydro-19(R)-19-hydroxy-11-deoxy-PGE$_1$, amide,
2,3-didehydro-19(R)-19-hydroxy-11-deoxy-16,16-, difluoro-PGE$_1$, amide,
2,3-didehydro-19(R)-19-hydroxy-11-deoxy-15(S)-15-methyl-PGE$_1$, amide,
2,3-didehydro-19(R)-19-hydroxy-11-deoxy-11α-hydroxymethyl-PGE$_1$, amide,
2,3-didehydro-19(R)-19-hydroxy-11-deoxy-11α-hydroxymethyl-16,16-difluoro-PGE$_1$, amide,
2,3-didehydro-19(R)-19-hydroxy-11-deoxy-11α-hydroxymethyl-15(S)-15-methyl-PGE$_1$, amide,
2,3-didehydro-19(R)-19-hydroxy-9-deoxo-9-methylene-PGE$_1$, amide,
2,3-didehydro-19(R)-19-hydroxy-9-deoxo-9-methylene-16,16-difluoro-PGE$_1$, amide,
2,3-didehydro-19(R)-19-hydroxy-9-deoxo-9-methylene-15(S)-15-methyl-PGE$_1$, amide,
2,3-didehydro-19(R)-19-hydroxy-9-deoxo-9-methylene-11-deoxy-PGE$_1$, amide,
2,3-didehydro-19(R)-19-hydroxy-9-deoxo-9-methylene-11-deoxy-16,16-difluoro-PGE$_1$, amide,
2,3-didehydro-19(R)-19-hydroxy-9-deoxo-9-methylene-11-deoxy-15(S)-15-methyl-PGE$_1$, amide,
19(R)-19-hydroxyPGF$_{1\alpha}$, amide,
16,16-dimethyl-19(R)-19-hydroxy-PGF$_{1\alpha}$, amide,
16,16-difluoro-19(R)-19-hydroxy-PGF$_{1\alpha}$, amide,
13,14-dihydro-19(R)-19-hydroxy-PGF$_{1\alpha}$, amide,
11-deoxy-19(R)-19-hyroxy-PGF$_{1\alpha}$, amide,
11-deoxy-16,16-dimethyl-19(R)-19-hydroxy-PGF$_{1\alpha}$, amide,
11-deoxy-16,16-difluoro-19(R)-19-hydroxy-PGF$_{1\alpha}$, amide, 11-deoxy-13,14-dihydro-19(R)-19-hydroxy-PGF$_{1\alpha}$, amide,
11-deoxy-11α-hydroxymethyl-19(R)-19-hydroxy-PGF$_{1\alpha}$, amide,
11-deoxy-11α-hydroxymethyl-16,16-dimethyl-19(R)-19-hydroxy-PGF$_{1\alpha}$, amide,
11-deoxy-11α-hydroxymethyl-16,16-difluoro-19(R)-19-hydroxy-PGF$_{1\alpha}$, amide,
11-deoxy-11α-hydroxymethyl-13,14-dihydro-19(R)-19-hyroxy-PGF$_{1\alpha}$, amide,
19(R)-19-hydroxy-PGF$_{1\beta}$, amide,
16,16-dimethyl-19(R)-19-hydroxy-PGF$_{1\beta}$, amide,
16,16-difluoro-19(R)-19-hydroxy-PGF$_{1\beta}$, amide,
13,14-dihydro-19(R)-19-hydroxy-PGF$_{2\beta}$, amide,
11-deoxy-19(R)-19-hydroxy-PGF$_{1\beta}$, amide,
11-deoxy-16,16-dimethyl-19(R)-19-hydroxy-PGF$_{1\beta}$, amide,
16,16-difluoro-19(R)-19-hydroxy-PGF$_{1\beta}$, amide,
11-deoxy-13,14-dihydro-19-(R)-19-hydroxy-PGF$_{1\beta}$, amide,
11-deoxy-11α-hydroxymethyl-19(R)-19-hydroxy-PGF$_{1\beta}$, amide,
11-deoxy-11α-hydroxymethyl-16,16-dimethyl-19(R)-19-hydroxy-PGF$_{1\beta}$, amide,
11-deoxy-11α-hydroxymethyl-16,16-difluoro-19(R)-19-hydroxy-PGF$_{1\beta}$, amide,
11-deoxy-11α-hydroxymethyl-13,14-dihydro-19(R)-19-hydroxy-PGF$_{1\beta}$, amide,
19(R)-19-hydroxy-PGE$_1$, amide,
16,16-dimethyl-19(R)-19-hydroxy-PGE$_1$, amide,
16,16-difluoro-19(R)-19-hydroxy-PGE$_1$, amide,
13,14-dihydro-19(R)-19-hydroxy-PGE$_1$, amide,
11-deoxy-19(R)-19-hydroxy-PGE$_1$, amide,
11-deoxy-16,16-dimethyl-19(R)-19-hydroxy-PGE$_1$, amide,
11-deoxy-16,16-difluoro-19(R)-19-hydroxy-PGE$_1$, amide,
11-deoxy-13,14-dihydro-19(R)-19-hydroxy-PGE$_1$, amide,
11-deoxy-11α-hydroxymethyl-19(R)-19-hydroxy-PGE$_1$, amide,
11-deoxy-11α-hydroxymethyl-16,16-dimethyl-19(R)-19-hydroxy-PGE$_1$, amide,
11-deoxy-11α-hydroxymethyl-16,16-difluoro-19(R)-19-hydroxy-PGE$_1$, amide,
11deoxy-11α-hydroxymethyl-13,14-dihydro-19(R)-19-hydroxy-PGE$_1$, amide,
9-deoxo-9-methylene-19(R)-19-hydroxy-PGE$_1$, amide,
9-deoxo-9-methylene-16,16-dimethyl-19(R)-19-hydroxy-PGE$_1$, amide,
9-deoxo-9-methylene-16,16-difluoro-19(R)-19-hydroxy-PGE$_1$, amide,
9-deoxo-9-methylene-13,14-dihydro-19(R)-19-hydroxy-PGE$_1$, amide, 9-deoxo-9-methylene-11-deoxy-19(R)-19-hydroxy-PGE$_1$, amide,
9-deoxo-9-methylene-11-deoxy-16,16-dimethyl-19(R)-19-hydroxy-PGE$_1$, amide,
9-deoxo-9-methylene-11-deoxy-16,16-difluoro-19(R)-19-hydroxy-PGE$_1$, amide,
9-deoxo-9-methylene-11-deoxy-13,14-dihydro-19(R)-19-hydroxy-PGE$_1$, amide,
9-deoxo-9-methylene-11-deoxy-11α-hydroxymethyl-19(R)- 19-hydroxy-PGE$_1$, amide,
9-deoxo-9-methylene-11-deoxy-11α-hydroxymethyl-16,16-dimethyl-19(R)-19-hydroxy-PGE$_1$, amide,
9-deoxo-9-methylene-11-deoxy-11α-hydroxymethyl-16,16-difluoro-19(R)-19-hydroxy-PGE$_1$, amide,
9-deoxo-9-methylene-11-deoxy-11α-hydroxymethyl-13,14-dihydro-19(R)-19-hydroxy-PGE$_1$, amide, The compounds of the present invention are particularly useful for including prostaglandin-like biological effects, as is described in Ser. No. 025,899. Uses of compounds in accordance with the present invention include, therefore, anti-asthmatic indications.

I claim:

1. A compound of the formula

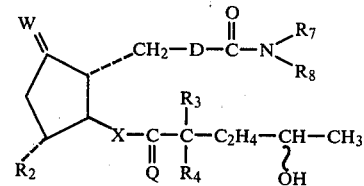

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)$_3$—CH=CH—,
(5) —(CH$_2$)$_3$—(CH$_2$)$_g$—CH$_2$—,
(6) —(CH$_2$)$_3$—CH$_2$—CF$_2$—,
(7) —(CH$_2$)$_3$—O—CH$_2$—,
(8) —(CH$_2$)$_2$—O—(CH$_2$)$_2$—,
(9) —CH$_2$—O—(CH$_2$)$_3$—,
(10) —(m—ph)—(CH$_2$)$_2$—, or
(11) —(m—ph)—O—CH$_2$—
wherein m—ph is inter-meta-phenylene, and wherein g is zero, one, two, or three; wherein Q is α—OH:β—R$_5$ or α—R$_5$:β—OH, wherein R$_5$ is hydrogen or methyl, wherein one of R$_7$ and R$_8$ is hydrogen and the other is —SO$_2$R$_{29}$ or wherein R$_7$ and R$_8$ are hydrogen, alkyl of one to 12 carbon atoms, inclusive, benzyl, or phenyl, being the same or different; wherein R$_{29}$ is hydrogen, alkyl of one to 12 carbon atoms, inclusive, aralkyl of 7 to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl of one to 4 carbon atoms, inclusive; wherein R$_2$ is hydrogen, hydroxyl, or hydroxymethyl; wherein R$_3$ and R$_4$ are hydrogen, methyl, or fluoro, being the same or different, with the proviso that one of R$_3$ and R$_4$ is fluoro only when the other is hydrogen or fluoro;

wherein W is oxo, methylene, α—OH:β—H, or α—H:β—OH; and wherein X is cis— or trans—CH=CH—, —C≡C—, or —CH$_2$CH$_2$—.

2. A compound according to claim 1, wherein g is one or three.

3. A compound according to claim 2, wherein D is cis—CH=CH—CH$_2$—(CH$_2$)$_g$—CH$_2$—.

4. A compound according to claim 3, wherein W is

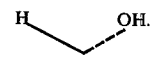

5. A compound according to claim 4, wherein R$_2$ is hydroxyl and X is trans—CH=CH—.

6. 19(R)-19-hydroxy-PGF$_{2\alpha}$, amide, a compound according to claim 5.

7. A compound according to claim 4, wherein R$_2$ is hydrogen and X is trans—CH=CH—.

8. 11-deoxy-19(R)-19-hydroxymethyl-11-deoxy-19(R)-19-hydroxy-PGF $2_\alpha$, amide, a compound according to claim 7.

9. A compound according to claim 4, wherein $R_2$ is hydroxymethyl and X is trans—CH=CH—.

10. 11-deoxy-11α-hydroxymethyl-19(R)-19-hydroxy-PGF$_{2\alpha}$, amide, a compound according to claim 9.

11. A compound according to claim 3, wherein W is

12. A compound according to claim 11, wherein $R_2$ is hydroxyl and X is trans—CH=CH—.

13. 19(R)-19-hydroxy-PGF$_{2\beta}$, amide, a compound according to claim 12.

14. A compound according to claim 11, wherein $R_2$ is hydrogen and X is trans—CH=CH—.

15. 11-deoxy-19(R)-hydroxy-PGF$_{2\beta}$, amide, a compound according to claim 14.

16. A compound according to claim 11, wherein $R_2$ is hydroxymethyl and X is trans—CH=CH—.

17. 11-deoxy-11α-hydroxymethyl-19(R)-19-hydroxy-PGF$_{2\beta}$, amide, a compound according to claim 16.

18. A compound according to claim 3, wherein W is

19. A compound according to claim 18, wherein $R_2$ is hydroxyl and X is trans—CH=CH—.

20. 19(R)-19-hydroxy-PGE$_2$, a compound according to claim 19.

21. A compound according to claim 19, wherein $R_2$ is hydrogen and X is trans—CH=CH—.

22. 11-deoxy-19(R)-19-hydroxy-PGE$_2$, amide, a compound according to claim 21.

23. A compound according to claim 18, wherein $R_2$ is hydroxymethyl and X is trans—CH=CH—.

24. 11-deoxy-11α-hydroxymethyl-19(R)-19-hydroxy-PGE$_2$, amide, a compound according to claim 23.

25. A compound according to claim 3, wherein W is

26. A compound according to claim 25, wherein $R_2$ is hydroxyl and X is trans—CH=CH—.

27. 9-deoxo-9-methylene-19(R)-19-hydroxy-PGE$_2$, amide, a compound according to claim 26.

28. A compound according to claim 25, wherein $R_2$ is hydrogen and X is trans—CH=CH—.

29. 9-deoxo-9-methylene-11-deoxy-19(R)-19-hydroxy-PGE$_2$, amide, a compound according to claim 28.

30. A compound according to claim 25, wherein $R_2$ is hydroxymethyl and X is trans—CH=CH—.

31. 9-deoxo-9-methylene-11-deoxy-11α-hydroxymethyl-19(R)-19-hydroxy-PGE$_2$, amide, a compound according to claim 30.

32. A compound according to claim 2, wherein D is cis—CH$_2$—CH=CH—CH$_2$—CH$_2$—.

33. A compound according to claim 32, wherein W is

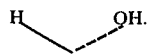

34. A compound according to claim 33, wherein $R_2$ is hydroxyl.

35. A compound according to claim 34, wherein X is trans—CH=CH—.

36. 4,5-didehydro-19(R)-19-hydroxy-PGF$_{1\alpha}$, amide, a compound according to claim 35.

37. 4,5-didehydro-19(R)-19-hydroxy-15(S)-15-methyl-PGF$_{1\alpha}$, amide, a compound according to claim 35.

38. A compound according to claim 34, wherein X is —C≡C—.

39. 4,5,13,14,-tetradehydro-19(R)-19-hydroxy-PGF$_{1\alpha}$, amide, a compound according to claim 38.

40. 4,5,13,14-tetradehydro-19(R)-19-hydroxy-16,16-difluoro-PGF$_{1\alpha}$, amide, a compound according to claim 38.

41. A compound according to claim 33, wherein $R_2$ is hydrogen.

42. A compound according to claim 41, wherein X is trans—CH=CH—.

43. 4,5-didehydro-19(R)-19-hydroxy-11-deoxy-PGF$_{1\alpha}$, amide, a compound according to claim 42.

44. 4,5-didehydro-19(R)-19-hydroxy-11-deoxy-15(S)-15-methyl-PGF$_{1\alpha}$, amide, a compound according to claim 42.

45. A compound according to claim 41, wherein X is —C≡C—.

46. 4,5,13,14-tetradehydro-19(R)-19-hydroxy-11-deoxy-PGF$_{1\alpha}$, amide, a compound according to claim 45.

47. 4,5,13,14-tetradehydro-19(R)-19-hydroxy-11-deoxy-16,16-difluoro-PGF$_{1\alpha}$, amide, a compound according to claim 45.

48. A compound according to claim 33, wherein $R_2$ is hydroxymethyl.

49. A compound according to claim 48, wherein X is trans—CH=CH—.

50. 4,5-dideoxy-19(R)-19-hydroxy-11-deoxy-11α-hydroxy-methyl-PGF$_{1\alpha}$, amide, a compound according to claim 49.

51. 4,5-dideoxy-19(R)-19-hydroxy-11-deoxy-11α-hydroxy-methyl-15(S)-15-methyl-PGF$_{1\alpha}$, amide, a compound according to claim 49.

52. A compound according to claim 48, wherein X is —C≡C—.

53. 4,5,13,14-tetradehydro-19(R)-19-hydroxy-11-deoxy-11α-hydroxymethyl-PGF$_{1\alpha}$, amide, a compound according to claim 52.

54. 4,5,13,14-tetradehydro-19(R)-19-hydroxy-11-deoxy-11α-hydroxymethyl-16,16-difluoro-PGF$_{1\alpha}$, amide, a compound according to claim 52.

55. A compound according to claim 32, wherein W is

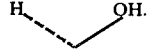

56. A compound according to claim 55, wherein $R_2$ is hydroxyl.

57. A compound according to claim 56, wherein X is trans—CH=CH—.

58. 4,5-didehydro-19(R)-19-hydroxy-PGF$_{1\beta}$, amide, a compound according to claim 57.

59. 4,5-didehydro-19(R)-19-hydroxy-15(S)-15-methyl-PGF$_{1\beta}$, amide, a compound according to claim 57.

60. A compound according to claim 56, wherein X is —C≡C—.

61. 4,5,13,14-tetradehydro-19(R)-19-hydroxy-PGF$_{1\beta}$, amide, a compound according to claim 60.

62. 4,5,13,14-tetradehydro-19(R)-19-hydroxy-16,16-difluoro-PGF$_{1\beta}$, amide, a compound according to claim 60.

63. A compound according to claim 55, wherein R$_2$ is hydrogen.

64. A compound according to claim 63, wherein X is trans—CH=CH—.

65. 4,5-didehydro-19(R)-19-hydroxy-11-deoxy-PGF$_{1\beta}$, a compound according to claim 64.

66. 4,5-didehydro-19(R)-19-hydroxy-11-deoxy-15(S)-15-methyl-PGF$_{1\beta}$, amide, a compound according to claim 64.

67. A compound according to claim 63, wherein X is —C≡C—.

68. 4,5,13,14-tetradehydro-19(R)-19-hydroxy-11-deoxy-PGF$_{1\beta}$, amide, a compound according to claim 67.

69. 4,5,13,14-tetradehydro-19(R)-19-hydroxy-11-deoxy-16,16-difluoro-PGF$_{1\beta}$, amide, a compound according to claim 67.

70. A compound according to claim 55, wherein R$_2$ is hydroxymethyl.

71. A compound according to claim 70, wherein X is trans—CH=CH—.

72. 4,5-didehydro-19(R)-19-hydroxy-11-deoxy-11α-hydroxy-methyl-PGF$_{1\beta}$, amide, a compound according to claim 71.

73. 4,5-didehydro-19(R)-19-hyroxy-11-deoxy-11α-hydroxy-methyl-15(S)-15-methyl-PGF$_{1\beta}$, amide, a compound according to claim 71.

74. A compound according to claim 70, wherein X is —C≡C—.

75. 4,5,13,14-tetradehydro-19(R)-19-hydroxy-11-deoxy-11α-hydroxymethyl-PGF$_{1\beta}$, amide, a compound according to claim 74.

76. 4,5,13,14-tetradehydro-19(R)-19-hydroxy-11-deoxy-11α-hydroxymethyl-16,16-difluoro-PGF$_{1\beta}$, amide, a compound according to claim 74.

77. A compound according to claim 32, wherein W is $$\overset{O.}{\underset{\|}{}}$$

78. A compound according to claim 77, wherein R$_2$ is hydroxyl.

79. A compound according to claim 78, wherein X is trans—CH=CH—.

80. 4,5-didehydro-19(R)-19-hydroxy-PGE$_1$, amide, a compound according to claim 79.

81. 4,5-didehydro-19(R)-19-hydroxy-15(S)-15methyl-PGE$_1$, amide, a compound according to claim 79.

82. A compound according to claim 78, wherein X is —C≡C—.

83. 4,5,13,14-tetradehydro-19(R)-19-hydroxy-PGE$_1$, amide, a compound according to claim 82.

84. 4,5,13,14-tetradehydro-19(R)-19-hydroxy-16,16-difluoro-PGE$_1$, amide, a compound according to claim 82.

85. A compound according to claim 77, wherein R$_2$ is hydrogen.

86. A compound according to claim 85, wherein X is trans—CH=CH—.

87. 4,5-didehydro-19(R)-19-hydroxy-11-deoxy-PGE$_1$, a compound according to claim 86.

88. 4,5-didehydro-19(R)-19-hydroxy-11-deoxy-15(S)-15-methyl-PGE$_1$, amide, a compound according to claim 86.

89. A compound according to claim 85, wherein X is —C≡C—.

90. 4,5,13,14-tetradehydro-19(R)-19-hydroxy-11-deoxy-PGE$_1$, amide, a compound according to claim 89.

91. 4,5,13,14-tetradehydro-19(R)-19-hydroxy-11-deoxy-16,16-difluoro-PGE$_1$, amide, a compound according to claim 89.

92. A compound according to claim 77, wherein R$_2$ is hydroxymethyl.

93. A compound according to claim 92, wherein X is trans—CH=CH—.

94. 4,5-didehydro-19(R)-19-hydroxy-11-deoxy-11α-hydroxy-methyl-PGE$_1$, amide, a compound according to claim 93.

95. 4,5-didehydro-19(R)-19-hydroxy-11-deoxy-11α-hydroxy-methyl-15(S)-15-methyl-PGE$_1$, amide, a compound according to claim 93.

96. A compound according to claim 92, wherein X is —C≡C—.

97. 4,5,13,14-tetradehydro19(R)-19-hydroxy-11-deoxy-11α-hydroxymethyl-PGE$_1$, amide, a compound according to claim 96.

98. 4,5,13,14-tetradehydro-19(R)-19-hydroxy-11-deoxy-11α-hydroxymethyl-16,16-di-fluoro-PGE$_1$, amide, a compound according to claim 96.

99. A compound according to claim 32, wherein W is $$\overset{CH_2.}{\underset{\|}{}}$$

100. A compound according to claim 99, wherein R$_2$ is hydroxyl.

101. A compound according to claim 100, wherein X is trans—CH=CH—.

102. 4,5-didehydro-19(R)-19-hydroxy-9-deoxo-9-methylene-PGE$_1$, amide, a compound according to claim 101.

103. 4,5-didehydro-19(R)-19-hydroxy-9-deoxo-9-methylene-15(S)-15-methyl-PGE$_1$, amide, a compound according to claim 101.

104. A compound according to claim 100, wherein X is —C≡C—.

105. 4,5,13,14-tetradehydro-19(R)-19-hydroxy-9-deoxo-9-methylene-PGE$_1$, amide, a compound according to claim 104.

106. 4,5,13,14-tetradehydro-19(R)-19-hydroxy-9-deoxo-9-methylene-16,16-difluoro-PGE$_1$, amide, a compound according to claim 108.

107. A compound according to claim 99, wherein R$_2$ is hydrogen.

108. A compound according to claim 107, wherein X is trans—CH=CH—.

109. 4,5-didehydro-19(R)-19-hydroxy-9-methylene-11-deoxy-PGE$_1$, a compound according to claim 108.

110. 4,5-didehydro-19(R)-19-hydroxy-9-deoxo-9-methylene-15(S)-15-methyl-PGE$_1$, amide, a compound according to claim 108.

111. A compound according to claim 107, wherein X is —C≡C—.

112. 4,5,13,14-tetradehydro-19(R)-19-hydroxy-9-deoxo-9-methylene-11-deoxy-PGE$_1$, amide, a compound according to claim 111.

113. 4,5,13,14-tetradehydro-19(R)-19-hydroxy-9-deoxo-9-methylene-11-deoxy-16,16-difluoro-PGE$_1$, amide, a compound according to claim 111.

114. A compound according to claim 99, wherein R$_2$ is hydroxymethyl.

115. A compound according to claim 114, wherein X is trans—CH═CH—.

116. 4,5-didehydro-19(R)-19-hydroxy-9-deoxo-9-methylene-11-deoxy-11α-hydroxymethyl-PGE$_1$, amide, a compound according to claim 115.

117. 4,5-didehydro-19(R)-19-hydroxy-9-deoxo-9-methylene-11-deoxy-11α-hydroxymethyl-15(S)-15-methyl-PGE$_1$, amide, a compound according to claim 115.

118. A compound according to claim 114, wherein X is —C≡C—.

119. 4,5,13,14-tetradehydro-19(R)-19-hydroxy-9-deoxo-9-methylene-11-deoxy-11α-hydroxymethyl-PGE$_1$, amide, a compound according to claim 118.

120. 4,5,13,14-tetradehydro-19(R)-19-hydroxy-9-deoxo-9-methylene-11-deoxy-11α-hydroxymethyl-16,16-difluoro-PGE$_1$, amide, a compound according to claim 118.

121. A compound according to claim 2, wherein D is trans—(CH$_2$)$_3$—CH═CH—.

122. A compound according to claim 121, wherein W is

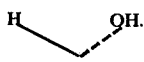

123. A compound according to claim 122, wherein R$_2$ is hydroxyl and X is trans—CH═CH—.

124. 2,3-didehydro-19(R)-19-hydroxy-PGF$_{1\alpha}$, amide, a compound according to claim 123.

125. 2,3-didehydro-19(R)-19-hydroxy-16,16-difluoro-PGF$_{1\alpha}$, amide, a compound according to claim 123.

126. 2,3-didehydro-19(R)-19-hydroxy-15(S)-15-methyl-PGF$_{1\alpha}$, amide, a compound according to claim 123.

127. A compound according to claim 122, wherein R$_2$ is hydrogen and X is trans—CH═CH—.

128. 2,3-didehydro-19(R)-19-hydroxy-11-deoxy-PGF$_{1\alpha}$, amide, a compound according to claim 127.

129. 2,3-didehydro-19(R)-19-hydroxy-11-deoxy-16,16-difluoro-PGF$_{1\alpha}$, amide, a compound according to claim 127.

130. 2,3-didehydro-19(R)-19-hydroxy-11deoxy-15(S)-15-methyl-PGF$_{1\alpha}$, amide, a compound according to claim 127.

131. A compound according to claim 122, wherein R$_2$ is hydroxymethyl, and X is trans—CH═CH—.

132. 2,3-didehydro-19(R)-19-hydroxy-11-deoxy-11α-hydroxymethyl-PGF$_{1\alpha}$, amide, a compound according to claim 131.

133. 2,3-didehydro-19(R)-19-hydroxy-11-deoxy-11α-hydroxymethyl-16,16-difluoro-PGF$_{1\alpha}$, amide, a compound according to claim 131.

134. 2,3-didehydro-19(R)-19-hydroxy-11-deoxy-11α-hydroxymethyl-15(S)-15-methyl-PGF$_{1\alpha}$, amide, a compound according to claim 131.

135. A compound according to claim 121, wherein W is

136. A compound according to claim 135, wherein R$_2$ is hydroxyl and X is trans—CH═CH—.

137. 2,3-didehydro-19(R)-19-hydroxy-PGF$_{1\beta}$, amide, a compound according to claim 136.

138. 2,3-didehydro-19(R)-19-hydroxy-16,16-difluoro-PGF$_{1\beta}$, amide, a compound according to claim 136.

139. 2,3-didehydro-19(R)-19-hydroxy-15(S)-15-methyl-PGF$_{1\beta}$, amide, a compound according to claim 136.

140. A compound according to claim 135, wherein R$_2$ is hydrogen and X is trans—CH═CH—.

141. 2,3-didehydro-19(R)-19-hydroxy-11-deoxy-PGF$_{1\beta}$, a compound according to claim 140.

142. 2,3-didehydro-19(R)-19-hydroxy-11-deoxy-16,16-difluoro-PGF$_{1\beta}$, amide, a compound according to claim 140.

143. 2,3-didehydro-19(R)-19-hydroxy-11-deoxy-15(S)-15-methyl-PGF$_{1\beta}$, amide, a compound according to claim 140.

144. A compound according to claim 135, wherein R$_2$ is hydroxymethyl, and X is trans—CH═CH—.

145. 2,3-didehydro-19(R)-19-hydroxy-11-deoxy-11α-hydroxymethyl-PGF$_{1\beta}$, amide, a compound according to claim 144.

146. 2,3-didehydro-19(R)-19-hydroxy-11-deoxy-11α-hydroxymethyl-16,16-difluoro-PGF$_{1\beta}$, amide, a compound according to claim 144.

147. 2,3-didehydro-19(R)-19-hydroxy-11-deoxy-11α-hydroxymethyl-15(S)-15-methyl-PGF$_{1\beta}$, amide, a compound according to claim 144.

148. A compound according to claim 121, wherein W is

149. A compound according to claim 148, wherein R$_2$ is hydroxyl and X is trans—CH═CH—.

150. 2,3-didehydro-19(R)-19-hydroxy-PGE$_1$, amide, a compound according to claim 149.

151. 2,3-didehydro-19(R)-19-16,16-difluoro-PGE$_1$, amide, a compound according to claim 149.

152. 2,3-didehydro-19(R)-19-hydroxy-15(S)-15-methyl-PGE$_1$, amide, a compound according to claim 149.

153. A compound according to claim 148, wherein R$_2$ is hydrogen and X is trans—CH═CH—.

154. 2,3-didehydro-19(R)-19-hydroxy-11-deoxy-PGE$_1$, amide, a compound according to claim 153.

155. 2,3-didehydro-19(R)-19-hydroxy-11-deoxy-16,16-difluoro-PGE$_1$, amide, a compound according to claim 153.

156. 2,3-didehydro-19(R)-19-hydroxy-11-deoxy-15(S)-15-methyl-PGE$_1$, amide, a compound according to claim 153.

157. A compound according to claim 148, wherein R$_2$ is hydroxymethyl, and X is trans—CH═CH—.

158. 2,3-didehydro-19(R)-19-hydroxy-11deoxy-11α-hydroxymethyl-PGE$_1$, amide, a compound according to claim 157.

159. 2,3-didehydro-19(R)-19-hydroxy-11-deoxy-11α-hydroxymethyl-16,16-difluoro-PGE$_1$, amide, a compound according to claim 157.

160. 2,3-didehydro-19(R)-19-hydroxy-11-deoxy-11α-hydroxymethyl-15(S)-15-methyl-PGE$_1$, amide, a compound according to claim 157.

161. A compound according to claim 121, wherein W is

162. A compound according to claim 161, wherein R$_2$ is hydroxyl and X is trans—CH=CH—.

163. 2,3-didehydro-19(R)-19-hydroxy-9-deoxo-9-methylene-PGE$_1$, amide, a compound according to claim 162.

164. 2,3-didehydro-19(R)-19-hydroxy-9-deoxo-9-methylene-16,16-difluoro-PGE$_1$, amide, a compound according to claim 162.

165. 2,3-didehydro-19(R)-19-hydroxy-9-deoxo-9-methylene-15(S)-15-methyl-PGE$_1$, amide, a compound according to claim 162.

166. A compound according to claim 161, wherein R$_2$ is hydrogen and X is trans—CH=CH—.

167. 2,3-didehydro-19(R)-19-hydroxy-9-deoxo-9-methylene-11-deoxy-PGE$_1$, amide, a compound according to claim 166.

168. 2,3-didehydro-19(R)-19-hydroxy-9-deoxo-9-methylene-11-deoxy-16,16-difluoro-PGE$_1$, amide, a compound according to claim 166.

169. 2,3-didehydro-19(R)-19-hydroxy-9-deoxo-9-methylene-11-deoxy-15(S)-15-methyl-PGE$_1$, amide, a compound according to claim 166.

170. A compound according to claim 161, wherein R$_2$ is hydroxymethyl, and X is trans—CH=CH—.

171. 2,3-didehydro-19(R)-19-hydroxy-9-deoxo-9-methylene-11-deoxy-11α-hydroxymethyl-PGE$_1$, amide, a compound according to claim 170.

172. 2,3-didehydro-19(R)-19-hydroxy-9-deoxo-9-methylene-11-deoxy-11α-hydroxymethyl-16,16-difluoro-PGE$_1$, a compound according to claim 170.

173. 2,3-didehydro-19(R)-19-hydroxy-9-deoxo-9-methylene-11-deoxy-11α-hydroxymethyl-15-(S)-15-methyl-PGE$_1$, amide, a compound according to claim 170.

174. A compound according to claim 2, wherein D is —(CH$_2$)$_3$—(CH$_2$)$_g$—CH$_2$—, wherein g is zero, one, two or three.

175. A compound according to claim 174, wherein g is one.

176. A compound according to claim 175, wherein W is

177. A compound according to claim 176, wherein R$_2$ is hydroxyl.

178. A compound according to claim 177, wherein X is trans—CH=CH—.

179. 19(R)-19-hydroxy-PGF$_{1α}$, amide, a compound according to claim 178.

180. 16,16-dimethyl-19(R)-19-hydroxy-PGF$_{1α}$, amide, a compound according to claim 178.

181. 16,16-difluoro-19(R)-19-hydroxy-PGF$_{1α}$, amide, a compound according to claim 178.

182. A compound according to claim 177, wherein X is —CH$_2$CH$_2$—.

183. 13,14-dihydro-19(R)-19-hydroxy-PGF$_{1α}$, amide, a compound according to claim 182.

184. A compound according to claim 176, wherein R$_2$ is hydrogen.

185. A compound according to claim 184, wherein X is trans—CH=CH—.

186. 11-deoxy-19(R)-19-hydroxy-PGF$_{1α}$, amide, a compound according to claim 185.

187. 11-deoxy-16,16-dimethyl-19(R)-19-hydroxy-PGF$_{1α}$, amide, a compound according to claim 185.

188. 11-Deoxy-16,16-difluoro-19(R)-19-hydroxy-PGF$_{1α}$, amide, a compound according to claim 185.

189. A compound according to claim 184, wherein X is —CH$_2$CH$_2$—.

190. 11-deoxy-13,14-dihydro-19(R)-19-hydroxy-PGF$_{1α}$, amide, a compound according to claim 189.

191. A compound according to claim 176, where R$_2$ is hydroxymethyl.

192. A compound according to claim 191, wherein X is trans—CH=CH—.

193. 11-deoxy-11α-hydroxymethyl-19(R)-19-hydroxy-PGF$_{1α}$, amide, a compound according to claim 192.

194. 11-deoxy-11α-hydroxymethyl-16,16-dimethyl-19(R)-19-hydroxy-PGF$_{1α}$, amide, a compound according to claim 192.

195. 11-deoxy-11α-hydroxymethyl-16,16-difluoro-19(R)-19-hydroxy-PGF$_{1α}$, amide, a compound according to claim 192.

196. A compound according to claim 191, wherein X is —CH$_2$CH$_2$—.

197. 11-deoxy-11α-hydroxymethyl-13,14-dihydro-19(R)-19-hydroxy-PGF$_{1α}$, amide, a compound according to claim 196.

198. A compound according to claim 175, wherein W is

199. A compound according to claim 198, wherein R$_2$ is hydroxyl.

200. A compound according to claim 199, wherein X is trans—CH=CH—.

201. 19(R)-19-hydroxy-PGF$_{1β}$, amide, a compound according to claim 200.

202. 16,16-dimethyl-19(R)-19-hydroxy-PGF$_{1β}$, amide, a compound according to claim 200.

203. 16,16-difluoro-19(R)-19-hydroxy-PGF$_{1β}$, amide, a compound according to claim 200.

204. A compound according to claim 199, wherein X is —CH$_2$CH$_2$—.

205. 13,14-dihydro-19(R)-19-hydroxy-PGF$_{2β}$, amide, a compound according to claim 204.

206. A compound according to claim 198, wherein R$_2$ is hydrogen.

207. A compound according to claim 206, wherein X is trans—CH=CH—.

208. 11-deoxy-19(R)-19-hydroxy-PGF$_{1β}$, a compound according to claim 207.

209. 11-deoxy-16,16-dimethyl-19(R)-19-hydroxy-PGF$_{1β}$, amide, a compound according to claim 207.

210. 16,16-difluoro-19(R)-19-hydroxy-PGF$_{1β}$, amide, a compound according to claim 207.

211. A compound according to claim 206, wherein X is —CH$_2$CH$_2$—.

212. 11-deoxy-13,14-dihydro-19(R)-19-hydroxy-PGF$_{1\beta}$, amide, a compound according to claim 211.

213. A compound according to claim 198, wherein R$_2$ is hydroxymethyl.

214. A compound according to claim 213, wherein X is trans—CH=CH—.

215. 11-deoxy-11α-hydroxymethyl-19(R)-19-hydroxy-PGF$_{1\beta}$, amide, a compound according to claim 214.

216. 11-deoxy-11α-hydroymethyl-16,16-dimethyl-19(R)-19-hydroxy-PGF$_{1\beta}$, amide, a compound according to claim 214.

217. 11-deoxy-11α-hydroxymethyl-16,16-difluoro-19(R)-19-hydroxy-PGF$_{1\beta}$, amide, a compound according to claim 214.

218. A compound according to claim 213, wherein X is —CH$_2$CH$_2$—.

219. 11-deoxy-11α-hydroxymethyl-13,14-dihydro-19(R)-19-hydroxy-PGF$_{1\beta}$, amide, a compound according to claim 218.

220. A compound according to claim 175, wherein W is $$\overset{O}{\underset{\|}{}}\cdot$$

221. A compound according to claim 220, wherein R$_2$ is hydroxyl.

222. A compound according to claim 221, wherein X is trans—CH=CH—.

223. 19(R)-19-hydroxy-PGE$_1$, amide, a compound according to claim 222.

224. 16,16-dimethyl-19(R)-19-hydroxy-PGE$_1$, amide, a compound according to claim 222.

225. 16,16-difluoro-19(R)-19-hydroxy-PGE$_1$, amide, a compound according to claim 222.

226. A compound according to claim 221, wherein X is —CH$_2$CH$_2$—.

227. 13,14-dihydro-19(R)-19-hydroxy-PGE$_1$, amide, a compound according to claim 226.

228. A compound according to claim 220, wherein R$_2$ is hydrogen.

229. A compound according to claim 228, wherein X is trans—CH=CH—.

230. 11-deoxy-19(R)-19-hydroxy-PGE$_1$, amide, a compound according to claim 229.

231. 11-deoxy-16,16-dimethyl-19(R)-19-hydroxy-PGE$_1$, amide, a compound according to claim 229.

232. 11-deoxy-16,16-difluoro-19(R)-19-hydroxy-PGE$_1$, amide, a compound according to claim 229.

233. A compound according to claim 228, wherein X is —CH$_2$CH$_2$—.

234. 11-deoxy-13,14-dihydro-19(R)-19-hydroxy-PGE$_1$, amide, a compound according to claim 233.

235. A compound according to claim 220, wherein R$_2$ is hydroxymethyl.

236. A compound according to claim 235, wherein X is trans—CH=CH—.

237. 11-deoxy-11α-hydroxymethyl-19(R)-19-hydroxy-PGE$_1$, amide, a compound according to claim 236.

238. 11-deoxy-11α-hydroxymethyl-16,16-dimethyl-19(R)-19-hydroxy-PGE$_1$, amide, a compound according to claim 236.

239. 11-deoxy-11α-hydroxymethyl-16,16-difluoro-19(R)-19-hydroxy-PGE$_1$, amide, a compound according to claim 236.

240. A compound according to claim 235, wherein X is —CH$_2$CH$_2$—.

241. 11-deoxy-11α-hydroxymethyl-13,14-dihydro-19(R)-19-hydroxy-PGE$_1$, amide, a compound according to claim 240.

242. A compound according to claim 175, wherein W is $$\overset{CH_2}{\underset{\|}{}}\cdot$$

243. A compound according to claim 242, wherein R$_2$ is hydroxyl.

244. A compound according to claim 243, wherein X is trans—CH=CH—.

245. 9-deoxo-9-methylene-19(R)-19-hydroxy-PGE$_1$, amide, a compound according to claim 244.

246. 9-deoxo-9-methylene-16,16-dimethyl-19(R)-19-hydroxy-PGE$_1$, amide, a compound according to claim 244.

247. 9-deoxo-9-methylene-16,16-difluoro-19(R)-19-hydroxy-PGE$_1$, amide, a compound according to claim 244.

248. A compound according to claim 243, wherein X is —CH$_2$CH$_2$—.

249. 9-deoxo-9-methylene-13,14-dihydro-19(R)-19-hydroxy-PGE$_1$, amide, a compound according to claim 248.

250. A compound according to claim 242, wherein R$_2$ is hydrogen.

251. A compound according to claim 250, wherein X is trans—CH=CH—.

252. 9-deoxo-9-methylene-11-deoxy-19(R)-19-hydroxy-PGE$_1$, amide, a compound according to claim 251.

253. 9-deoxo-9-methylene-11-deoxy-16,16-dimethyl-19(R)-19-hydroxy-PGE$_1$, amide, a compound according to claim 251.

254. 9-deoxo-9-methylene-11-deoxy-16,16-difluoro-19(R)-19-hydroxy-PGE$_1$, amide, a compound according to claim 251.

255. A compound according to claim 250, wherein X is —CH$_2$CH$_2$—.

256. 9-deoxo-9-methylene-11-deoxy-13,14-dihydro-19(R)-19-hydroxy-PGE$_1$, amide, a compound according to claim 255.

257. A compound according to claim 242, wherein R$_2$ is hydroxymethyl.

258. A compound according to claim 257, wherein X is trans—CH=CH—.

259. 9-deoxo-9-methylene-11-deoxy-11α-hydroxymethyl-19-(R)-19-hydroxy-PGE$_1$, amide, a compound according to claim 258.

260. 9-deoxo-9-methylene-11-deoxy-11α-hydroxymethyl-16,16-dimethyl-19(R)-19-hydroxy-PGE$_1$, amide, a compound according to claim 258.

261. 9-deoxo-9-methylene-11-deoxy-11α-hydroxymethyl-16,16-difluoro-19(R)-19-hydroxy-PGE$_1$,amide, a compound according to claim 258.

262. A compound according to claim 257, wherein X is —CH$_2$CH$_2$—.

263. 9-deoxo-9-methylene-11-deoxy-11α-hydroxymethyl-13,14-dihydro-19(R)-19-hydroxy-PGE$_1$, a compound according to claim 262.

* * * * *

UNITED STATES PATENT OFFICE
CERTIFICATE OF CORRECTION

Patent No. 4,264,522  Dated 28 April 1981

Inventor(s) John C. Sih

It is certified that error appears in the above-identified patent and that said Letters Patent are hereby corrected as shown below:

Column 1, line 49, "(m-ph) $(CH_2)_2$-," should read -- -(m-Ph)-$(CH_2)_2$-, --;
line 50, "(m-ph)-O-$CH_2$-" should read -- -(m-Ph)-O-$CH_2$- --;
Column 6, line 30 and 31, "-(m-ph)-" should read -- -(m-Ph)- --; line 32, "wherein m-ph is" should read -- wherein -(m-Ph)- is --;
Column 10, line 11 and 30, "-C C-" should read -- -C≡C- --; line 62, "according to claim 108" should read -- according to claim 104 --;

Column 12, line 50, "-19(R)-19-16,16-difluoro-" should read ---19(R)-19-hydroxy-16,16-difluoro- --;
Column 14, line 67, "16,16-difluoro-19(R)-" should read -- 11-Deoxy-16,16-difluoro-19(R)- --.

Signed and Sealed this

Eighteenth Day of August 1981

[SEAL]

Attest:

GERALD J. MOSSINGHOFF

Attesting Officer  Commissioner of Patents and Trademarks